US00RE35413E

United States Patent [19]

Mylchreest et al.

[11] E Patent Number: Re. 35,413

[45] Reissued Date of Patent: Dec. 31, 1996

[54] ELECTROSPRAY ION SOURCE WITH REDUCED NEUTRAL NOISE AND METHOD

[75] Inventors: Iain C. Mylchreest, Milpitas, Calif.; Mark E. Hail, Yardley, Pa.

[73] Assignee: Finnigan Corporation, San Jose, Calif.

[21] Appl. No.: 220,963

[22] Filed: Mar. 30, 1994

Related U.S. Patent Documents

Reissue of:

[64] Patent No.: 5,171,990
Issued: Dec. 15, 1992
Appl. No.: 703,471
Filed: May 17, 1991

[51] Int. Cl.[6] ..... B01D 59/44; H01J 49/00

[52] U.S. Cl. ..... 250/282; 250/288

[58] Field of Search ..... 250/281, 282, 250/288, 289

[56] References Cited

U.S. PATENT DOCUMENTS

| | | | |
|---|---|---|---|
| 4,300,044 | 11/1981 | Iribarne et al. | 250/288 |
| 4,542,293 | 9/1985 | Fenn et al. | 250/288 |
| 4,861,988 | 8/1989 | Henion et al. | 250/288 |
| 4,885,076 | 12/1989 | Smith et al. | 204/299 R |
| 4,963,735 | 10/1990 | Okamoto et al. | 250/288 |
| 4,994,165 | 2/1991 | Lee et al. | 204/299 R |
| 5,349,186 | 9/1994 | Ikonomou et al. | 250/288 |

OTHER PUBLICATIONS

Bruins, A. P., et al., "Ion Spray Interface for Combined Liquid Chromatography/Atmospheric Pressure Ionization Mass Spectrometry", *Analytical Chemistry*, 59(22):2642–2646 (1987). No Month.

*Primary Examiner*—Bruce C. Anderson
*Attorney, Agent, or Firm*—Flehr, Hohbach, Test, Albritton & Herbert

[57] ABSTRACT

An electrospray ion source having a capillary tube for directing ions from an ionizing region to an analyzing region including a skimmer in which the capillary tube is oriented to cause undesolvated droplets to strike the skimmer.

2 Claims, 2 Drawing Sheets

ELECTROSPRAY ION SOURCE WITH REDUCED NEUTRAL NOISE AND METHOD

Matter enclosed in heavy brackets [ ] appears in the original patent but forms no part of this reissue specification; matter printed in italics indicates the additions made by reissue.

BRIEF DESCRIPTION OF THE INVENTION

This invention relates generally to electrospray ion sources and more particularly to sources having reduced neutral noise.

BACKGROUND OF THE INVENTION

The electrospray process consists of flowing sample liquid through a small tube or capillary which is maintained at a high voltage with respect to a nearby surface. The liquid is dispersed into fine electrically charged droplets or by the voltage gradient of the tip of the capillary. The ionization mechanism involves the desorption at atmospheric pressure of ions from the fine electrically charged particles. In many cases, a heated gas is flowed in counter-current to the electrospray to enhance dissolution of the electrospray droplets. The ions created by the electrospray are then mass analyzed in a mass analyzer such as a mass spectrometer.

Under the appropriate conditions, the electrospray resembles a symmetrical cone consisting of a very fine mist (or fog) of droplets (ca. 1 μm diameter). Excellent sensitivity and ion current stability can be obtained if the fine mist is produced. Unfortunately, the electrospray "quality" is highly dependent on the bulk properties of the solution being analyzed. The most important of which are surface tension and conductivity. A poor quality electrospray may contain larger droplets (>10 μm diameter) or a non-dispersed droplet stream.

The use of sheath liquid and a focusing gas are often used to insure stable sprays when electrospraying high aqueous content sample solutions. One type of electrospray interface apparatus includes an inner needle for transferring a liquid sample to an ionizing region at one end of the needle, a first outer tube surrounding and spaced from said needle for flowing a liquid past the tip of said needle, and a second outer tube surrounding the first tube to define a second cylindrical space for flowing a gas past the end of said first tube and needle to focus the electrospray.

In U.S. Pat. No. 4,542,293 there is described the use of a tube made of an electrical insulator for conducting ions in the ionizing electrospray region at atmospheric pressure and a low pressure region. A glass or quartz capillary is suitable. Ions and gas are caused to flow from the ionization region through the tube into the low pressure region where free jet expansion occurs. A conductive coating is formed on the ends of the insulating tube and a voltage is applied thereacross to accelerate ions which flow through the tube. A conducting skimmer is disposed adjacent the end of the tube and is maintained at a voltage which causes further acceleration of the ions through and into a lower pressure region including focusing lenses and analyzing apparatus.

The electrospray process employing a sheath liquid and focusing gas provides small droplets or particle which are desolvated by the addition of a counter current drying gas. Occasionally, larger undesolvated droplets or particles will traverse into the capillary and will acquire substantial kinetic energy which will allow it to pass through the skimmer and into the lens region. The droplets or particles impinge upon surfaces and forms secondary ions. These ions are random and cause noise to be observed at the analyzer detector, thereby decreasing the signal to noise levels and producing noise spikes in the ion chromatogram.

OBJECTS AND SUMMARY OF THE INVENTION

It is a general object of this invention to provide an ion source and method in which high velocity droplets or particles are prevented from flowing into the lens region of an associated analyzer.

It is another object of the invention to provide an ion source which includes a skimmer and means for directing high velocity droplets or particles away from the skimmer aperture.

The foregoing and other objects of this invention are achieved in an electrospray ion source of the type which includes a tube communicating between the ionizing region and a low pressure region with a skimmer having an aperture through which ions pass, the skimmer separating the low pressure region from a lower pressure region which includes lenses and an analyzer, where analysis is carried out. The capillary is oriented so that undesolvated droplets or particles travelling through the capillary are prevented from passing through the skimmer aperture into the analysis region.

BRIEF DESCRIPTION OF THE DRAWINGS

The foregoing and other objects of the invention will be more clearly understood from the description to follow when read in conjunction with the accompanying drawings of which.

DETAILED DESCRIPTION OF THE INVENTION

Figure 1:
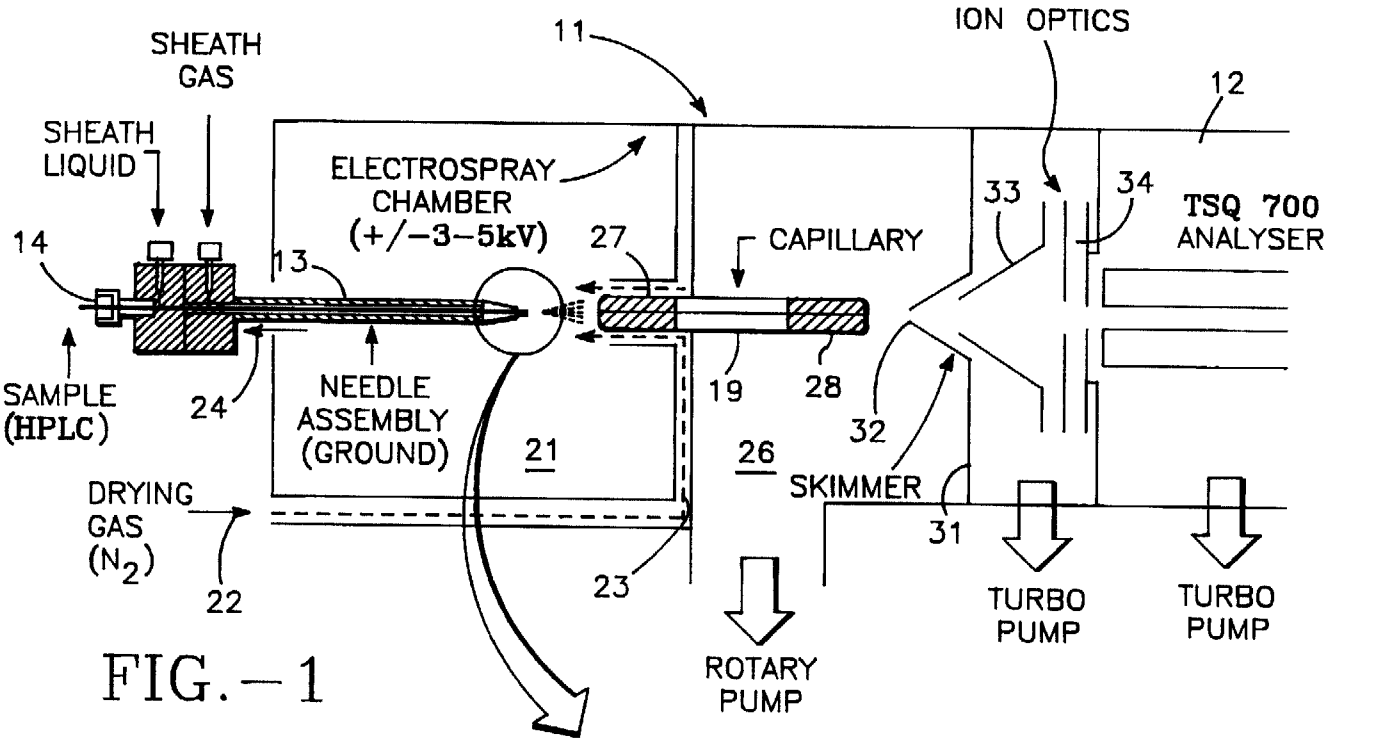
FIG. 1 shows an electrospray ion source coupled to an analyzing region via a capillary tube.

Referring to FIG. 1, an electrospray ion source 11 is schematically shown as associated with an analyzer chamber 12. The source includes an input needle 13 into which a liquid sample 14 is introduced.

Figure 2:
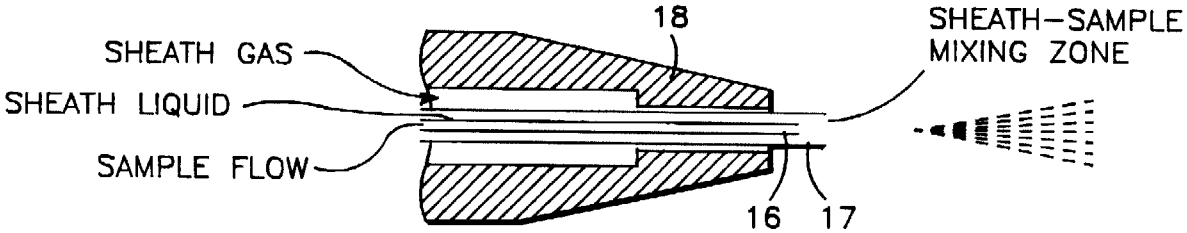
FIG. 2 is an enlarged view of the region 2—2 of FIG. 1.

Referring particularly to FIG. 2, the needle includes an inner tube 16 in which the liquid sample is introduced. Surrounding the tube is a second tube 17 which defines with the first tube an annular region through which a liquid is introduced for mixing with the sample liquid to reduce the surface tension and form droplets. An outer tube 18 forms a second annulus through which a focusing gas is introduced to focus the droplets as they exit the needle towards a capillary tube 19. As previously explained, the needle, or capillary, is maintained at a high voltage with respect to the nearby surfaces forming the ionization chamber 21 and as the liquid is dispersed, the droplets or particles are charged by the voltage gradient at the tip of the capillary. The ionization mechanism involves the desorption at atmospheric pressure of ions from the fine electrically charged particles. A counter-flow of gas indicated by the arrow 22 enhances the desorption process. The gas flows through a chamber 23 past the end of the capillary 19 and exits the ionization chamber 21 as indicated schematically at 24.

A chamber 26 maintained at a lower pressure than the atmosphere pressure of the chamber 21 communicates with the ionization chamber via the capillary tube 19. Due to the differences in pressure, ions and gas are caused to flow through the capillary 19 into the chamber 26. A voltage is applied between conductive sleeves 27 and 28 to provide a voltage gradient. The end of the tube 19 is supported by, for example, three supports 29 disposed at 120° with respect to one another.

The end of the capillary is opposite a skimmer 31 which separates the low pressure region 26 from a lower pressure region in the analyzer 12. The skimmer includes a central orifice or aperture 32 which normally is aligned with the axis of the bore of the capillary. The skimmer is followed by ion optics which may comprise a second skimmer 33 and lenses 34, which direct ions into the analyzing chamber and into a suitable analyzer.

As described above, the solvated droplets or particles flow into the capillary and acquire kinetic energy which allows them to pass through the skimmer aperture 32 into the lens region including skimmer 33 and lenses 34. These droplets or particles impact on the surfaces of the skimmer 33 or the lenses 34 and create secondary ions. These ions are random and find their way into the detector and cause noise to be observed at the detector, thereby decreasing the signal-to-noise level and producing electronic spikes in the mass spectrum.

Figure 4:
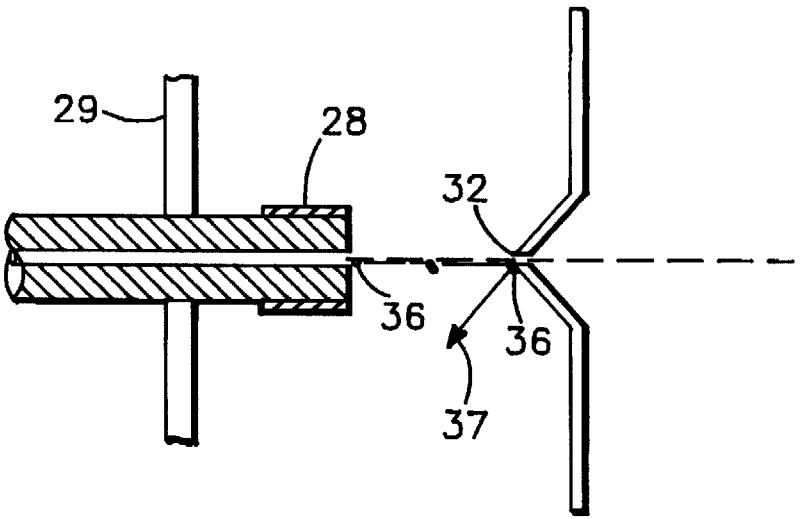
FIG. 4 is an enlarged view of the region 4—4 of FIG. 1.
Figure 3:
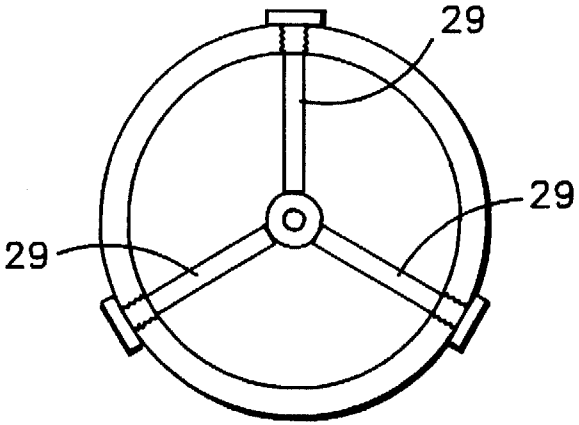
FIG. 3 is a sectional view taken along the line 3—3 of FIG. 1 showing the tube support.

In accordance with this invention, the axis of the capillary is altered or directed as shown in FIG. 4 by adjusting the supports 29 so that the axis is offset from the skimmer orifice or aperture. In this way, there is no alignment between the bore of the capillary and the orifice of the skimmer. The tendency is for the large droplets or particles to move to the center of the flow in the capillary and travel in a straight line. These droplets or particles traveling in a straight line strike the skimmer. This is illustrated in FIG. 4, which shows that large particles 36 travel a straight line and impinge upon the skimmer 31. The droplets or particles are thereafter pumped away by the vacuum pump associated with the chamber 26 as illustrated by the arrow 37. The realignment of the axis of the capillary tube does not cause any significant loss in the observed signal intensity of the ions being analyzed. This is due to the fact that the analyzed ions and gases undergo a free jet expansion and are deviated from the axis to travel through the orifice or aperture 32.

Thus, there has been provided a method and apparatus for reducing neutral noise in an electrospray.

What is claimed is:

[1. An ion source of the type which includes an ionization chamber and an adjacent low pressure region including a skimmer having an orifice, a capillary tube having an axial bore communicating between the ionization chamber and the low pressure region whereby ions and gases in said ionization chamber flows through said bore into said low pressure region, directing the axis of the capillary tube away from the skimmer orifice whereby droplets and/or particles flowing through the bore are not allowed to pass through the skimmer, while ions are transmitted into the low pressure chamber.]

[2. An electrospray ion source as in claim 1 in which said ionization chamber includes means for electrospraying a sample to be analyzed.]

*3. A method of operating an ion source, said ion source including a low pressure chamber having a skimmer with an orifice and a capillary tube having a bore with an axis, said method comprising the steps of:*

*desolvating charged droplets in said ion source to produce a flow of ions and undesolvated droplets;*

*causing said flow of ions and undesolvated droplets to flow from said bore along said axis of said bore into said low pressure chamber; and*

*offsetting said axis of said bore from said orifice of said skimmer so that said ions flow through said orifice while said undesolvated droplets impinge upon said skimmer.*

*4. A method of operating an ion source, said ion source including a low pressure chamber having a skimmer with an orifice, and means to communicate with the low pressure chamber, said method comprising the steps of:*

*desolvating charged droplets in said ion source to produce a flow of ions and undesolvated droplets;*

*causing said flow of ions and undesolvated droplets to flow from said communicating means along an axis of said communicating means into said low pressure chamber; and*

*offsetting said axis of said communicating means from said orifice of said skimmer so that said ions flow through said orifice while said undesolvated droplets impinge upon said skimmer.*

* * * * *